United States Patent [19]

Buchardt et al.

[11] Patent Number: 5,972,610
[45] Date of Patent: *Oct. 26, 1999

[54] USE OF NUCLEIC ACID ANALOGUES IN THE INHIBITION OF NUCLEIC ACID AMPLIFICATION

[76] Inventors: Ole Buchardt, deceased, late of Vaerlose, Denmark; by Dorte Buchardt, legal representative, Sondergaardsvej 73, DK-3500 Vaerlose, Denmark; Michael Egholm, 1231 Lexington Ridge Dr., Lexington, Mass. 02173; Peter Eigil Nielsen, Hjortevaenget 509, DK-2980 Kokkedal; Rolf Henrik Berg, Langelandsvej 20 B, 3.th, DK-2000 Fredericksberg, both of Denmark, DK-2000; Christopher John Stanley, 12A Cromwell Place, St. Ives, Huntingdon, Cambridgeshire, PE 17 4JB, United Kingdom, 4JB

[*] Notice: This patent is subject to a terminal disclaimer.

[21] Appl. No.: 08/947,317

[22] Filed: Oct. 8, 1997

Related U.S. Application Data

[62] Division of application No. 08/338,535, Mar. 10, 1995.

[30] Foreign Application Priority Data

Jun. 5, 1992 [GB] United Kingdom .................. 9211979

[51] Int. Cl.⁶ .............................. C12Q 1/68; C12P 19/34; C07H 21/04; C12N 15/00

[52] U.S. Cl. ............................. 435/6; 435/91.1; 435/91.2; 536/24.5; 935/77; 935/78

[58] Field of Search ............................. 435/6, 91.1, 91.2; 536/24.5; 935/77, 78

[56] References Cited

U.S. PATENT DOCUMENTS

| 4,683,195 | 7/1987 | Mullis et al. ................................ 435/6 |
| 4,988,617 | 1/1991 | Landegren et al. ......................... 435/6 |

OTHER PUBLICATIONS

Nielsen et al., Science, vol. 254, pp. 1497–1500, Dec. 6, 1991, "Sequence–Selective Recognition of DNA by Strand Displacement with a Thymine–Substituted Polyamide".

Meier et al., Angew. Chem. Int. Ed. Engl. vol. 31, No. 8, pp. 1008–1010, 1992, "Peptide Nucleic Acids (PNAs)—Unusual Properties of Nonionic Oligonucleotide Analogues".

*Primary Examiner*—Kenneth R. Horlick
*Assistant Examiner*—Joyce Tung
*Attorney, Agent, or Firm*—Nikaido Marmelstein Murray & Oram LLP

[57] ABSTRACT

The present invention relates to the use of nucleic acid analogues in blocking nucleic acid amplification procedures and to diagnostic and analytical techniques based thereon. Also included are kits for use in the conduct of nucleic acid amplification reactions.

26 Claims, 5 Drawing Sheets

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Primer.

<400> SEQUENCE: 1
aacagctatg accatg                                                       16

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer.

<400> SEQUENCE: 2
cacacaggaa acagctatga c                                                 21

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer.

<400> SEQUENCE: 3
gtaaaacgac ggccagt                                                      17

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Primer.

<400> SEQUENCE: 4
catccttttt tttttg                                                       16

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer.

<400> SEQUENCE: 5
tctagaacta gtggatc                                                      17

USE OF NUCLEIC ACID ANALOGUES IN THE INHIBITION OF NUCLEIC ACID AMPLIFICATION

This is a divisional application of Ser. No. 08/338,535, filed Mar. 10, 1995.

The present invention relates to the use of nucleic acid analogues in blocking nucleic acid amplification procedures and to diagnostic/analytical techniques based thereon.

Nucleic acid amplification techniques are now in widespread use. These include the "PCR" (polymerase chain reaction) procedures described in EP-A-0200362 and EP-A-0201184 which is the technique in most widespread use, but also the "LCR" (ligase chain reaction) described in EP-A-0320308 and the so-called "NASBA" or "3SR" technique which is described in "Proc. Natl. Acad. Sci. USA" Vol 87. pp 1874–1878 March 1990 and "Nature" Vol 350, No 6313. pp 91–92 Mar. 7th 1991.

A major problem in the use of these procedures in diagnostics is the production of false positives by the carry over of amplified nucleic acid sequences from previous reactions. As these procedures are capable of producing a positive result if even a single molecule containing the target sequence is present, it is of course very easy for such a false positive to occur. At present it is necessary for the reaction product of such procedures to be worked up before the success or failure of the amplification procedure can be determined. The involves contact between the reaction product and several pieces of laboratory equipment such as pipettes, as well as with personnel which can lead to traces of the amplification product being available to contaminate future runs.

Much effort is currently going into developing so called "intrinsic" procedures in which the success of the amplification reaction can be monitored without any handling of the amplification product and in an unopened reaction vessel.

New forms of nucleic acid analogue are described in Patent Co-operation Treaty application. No. PCT/EP92/01220 filed on May 22nd 1992 which selectively bind conventional nucleic acids of complementary sequence to form hybrids which are more stable against dehybridisation by heat than are similar hybrids between conventional nucleic acids. We have now found that it is possible to exploit this greater hybrid stability to block selectively nucleic acid amplification procedures. This technique may be used to prevent false positives in such amplification procedures. It may also be exploited as an essential part of certain diagnostics/analytical approaches.

In a first aspect the invention provides a method of inhibiting a nucleic acid amplification procedure comprising providing in said procedure an effective amount of a nucleic acid analogue sufficiently complementary to a sequence of nucleic acid participating in an essential manner in said amplification procedure to hybridises to said sequence sufficiently strongly to prevent the effective participation of said sequence in the amplification procedure. Thus this aspect of the invention includes a method of inhibiting a nucleic acid amplification procedure in which procedure each strand of a double stranded target nucleic acid has a region used as a template for one or more primers which is or are extended or linked to form a second template complementary to said template, wherein a nucleic acid analogue sufficiently complementary to a sequence of a said template or a said primer to hybridise therewith is provided and wherein said nucleic acid analogue hybridises sufficiently strongly to the respective template or primer to block primer template hybridisation or to block primer extension or primer linking under the conditions of the procedure.

Preferably, said procedure is a PCR or LCR or a 3SR procedure. "Anchored" and "inverted" PCR procedures are included.

The "double stranded target nucleic acid" which has in each strand a region acting as a template is not necessarily a starting material, nor need it necessarily be the direct object of desired amplification in the procedure.

In PCR the "double stranded target nucleic acid" will usually be incorporated in the starting material and it will generally be the amplification of at least one strand thereof which is desired. However, one can start a PCR reaction with only one DNA strand, the complementary strand being produced in the first cycle of primer extension. In later cycles, the "double stranded target nucleic acid" will be composed of products from previous cycles predominantly.

In LCR, the "double stranded target nucleic acid" will similarly initially normally be incorporated in the starting material and in later cycles will predominantly be the amplification product.

It is not necessarily the case that primers are hybridised to each strand in the same part of the amplification cycle or, indeed only after the double stranded target nucleic acid has been formed. Thus in the 3SR technique, a starting RNA strand is hybridised to a first primer which is extended as a complementary DNA strand by reverse transcriptase to form the "double stranded target nucleic acid" referred to. After destruction of the hybridised RNA strand by RNase H, a second primer is hybridised to the DNA strand and extended by reverse transcriptase to form a double stranded DNA molecule. Thus by this stage, both strands present in the DNA/RNA will have in their time been hybridised to a primer which has then been extended.

The first primer is so constructed that the DNA/DNA product includes a promoter for an RNA polymerase such as T7 RNA polymerase which using the DNA/DNA product as a template produces multiple RNA copies corresponding to the RNA starting material, which each in turn become starting materials for the first primer and reverse transcriptase to act upon.

Said amplification procedure may be conducted in the absence of said nucleic acid analogue to build-up a desired level of amplification product and said nucleic acid analogue may then be added.

Preferably the said nucleic acid analogue hybridises to said amplification product. This will shut down the amplification and can leave the products in the form of stable nucleic acid—nucleic acid analogue hybrids which are unable to act as templates if they contaminate a subsequent reaction. "Open" rather than "intrinsic" procedures are thereby rendered safe against carry over contamination.

Alternatively or additionally, apparatus to be used in an amplification procedure of said type can be treated with a solution containing said nucleic acid analogue to hybridise said analogue to any amplification product which may be present as a contamination, and the apparatus may be thereafter washed and used in a said amplification procedure, amplification in said procedure of any amplification product present initially as a contamination in said apparatus being prevented by said hybridisation to said analogue.

The invention includes therefore a method of preventing a nucleic acid amplification product from serving as a template in a subsequent amplification procedure, which method comprises hybridising thereto a nucleic acid analogue which forms therewith a hybrid which is stable under the conditions of the subsequent amplification procedure.

The invention also includes a method of preventing any nucleic acid amplification product which may be present in an environment from serving as a contaminating template in a subsequent amplification procedure for the nucleic acid, which method comprises treating the environment with a nucleic acid analogue which forms with said amplification product a hybrid which is stable under the conditions of said subsequent amplification procedure.

In practice, one may wash all or some equipment to be utilised in the procedure with a solution containing the nucleic acid analogue, e.g. in a hybridisation buffer, so as to form a stable hybrid, between the analogue and any nucleic acid present which contains the target sequence for the amplification. The hybrid formed with the nucleic acid analogue is sufficiently stable to withstand the conditions of the subsequent amplification procedure and the contaminant target sequence is thereby prevented from participating in such a procedure to produce a false positive.

The nucleic acid analogue for use in this and other aspects of the invention preferably contains from five to 20 nucleobase binding ligands e.g. from ten to fifteen ligands.

One may provide a nucleic acid analogue which is tailored to halt amplification of a specific nucleic acid sequence or one may provide a reagent containing a mixture of nucleic acid analogue sequences which will stop a number of different amplifications. Preferably, a reagent for this latter purpose contains a multiplicity or multitude of sequences. In the extreme, one may synthesise nucleic acid analogues using a mixture of monomer synthons (including ligands, complementary to each of the four DNA bases) in each step so as to construct molecules each containing a random sequence of ligands. A sufficient quantity of such a reagent should contain a sufficient number of molecules complementary to any amplification product to be able to inhibit any amplification procedure.

Generally, it will be preferred for each molecule of nucleic acid analogue in such a reagent to be at least a 10-mer, more preferably at least a 12-mer, e.g. a 15- to 20-mer.

The selective blocking of amplification procedures may be put to work more actively as part of a diagnostic process.

At present, when using methods such as PCR to amplify a sequence with a view to determining whether a particular sequence is present, such as a single base change from an alternative sequence (e.g. a single base mutation from the "normal" sequence in a gene), the procedures for detecting the sequence in the amplification product are laborious. These include sequencing the entire product to verify the presence of the altered base. They include also detecting an altered pattern of digestion products produced by one or more restriction enzymes if the change or changes in the gene sequence affect a restriction site. They also include hybridising to the product a labelled nucleic acid probe for the mutated sequence under conditions which are sufficiently stringent to differentiate between the possible sequences.

By designing a nucleic acid analogue capable of forming a stable hybrid with the PCR target sequence only if the mutation is present and providing said analogue to the sample nucleic acid under hybridising conditions, one may selectively inhibit the PCR reaction so that no exponential amplification takes place of the mutation containing sequence. This principle may be extended also to other amplification methods.

Thus, the invention includes a method of detecting the presence or absence of a target nucleic acid sequence comprising conducting an amplification procedure in which each strand of a double stranded nucleic acid having a region used as a template including that part of said nucleic acid in which said target sequence is located if present is amplified by hybridisation of one or more primers to said template and extension or linkage of said primers to form a second template complementary to said template, wherein a nucleic acid analogue is provided which is complementary to said target sequence and hybridises with a said template sufficiently strongly to block said amplification procedure when said target sequence is present but not otherwise.

If the nucleic acid analogue is present throughout the amplification reaction, amplification of the other strand of the target sequence will be linear rather than exponential so that no significant quantities of amplification product will be produced.

The presence of the target sequence may therefore be deduced from the failure of the amplification reaction, which may be PCR or LCR or 3SR, to produce a significant product level. The product of the reaction may for instance be run on a gel and failure to produce a band will indicate the presence of the sequence.

It will be desirable to include an internal control to guard against the reaction having failed for some other reason. Thus, preferably as a control, a second nucleic acid substrate capable of amplification by said amplification procedure using the same primers is included which undergoes amplification to produce a product different from the product of amplification of the target sequence.

The procedure may be carried out in this way to detect the presence of a particular base at a specific location, e.g. to demonstrate the presence of a specific single base mutation. A series of such analyses may be conducted side by side or sequentially to identify which if any of a range of possible mutations is present within a gene region by using in each analysis a nucleic acid analogue tailored to a respective mutation.

In the case of a mutation from a more common sequence, one may regard the mutation or the "normal" sequence as the "target nucleic acid sequence". Thus if the nucleic acid analogue is complementary to the mutated sequence, failure of the amplification demonstrates the presence of the mutation. Alternatively, one may use a nucleic acid analogue complementary to the "normal" sequence, whereupon failure of the amplification will demonstrate the presence of the "normal" sequence and successful amplification will show the presence of an unspecified mutation, i.e. the absence of the "normal" sequence.

Although it has been found that nucleic acid analogues such as the PNA's can block a PCR amplification reaction whether the PNA is directed to hybridise to a PCR primer binding site or to a nucleotide sequence in the template which is substantially removed from the. primer binding site, it is not the case that the choice of PNA/DNA hybridisation site is immaterial. Generally, the level of affinity between the PNA and the DNA template required to stop the PCR reaction is somewhat less when the PNA hybridises to the primer binding site or close to it. The affinity can be fine tuned by appropriate choice of PNA sequence length taking into account the particular base sequence involved, homopyrimidine regions binding most strongly.

Thus, it is possible to choose conditions such that two PCR reactions can be conducted on a single template simultaneously, one being used as a control and being impervious to the presence of a suitable PNA which will inhibit the other. Thus, if one employs a single forward primer in combination with two different reverse primers, one producing a longer and the other a shorter amplification product, one can direct the PNA to the binding site of the shorter product primer or close to it and prevent its respective PCR reaction without simultaneously inhibiting the longer product PCR reaction if one chooses the affinity of the PNA judiciously. If the PNA hybridisation site is one containing a single base pair mutation which one wishes to detect, one can arrange matters so that if the mutation is present PNA binds and only one PCR product is produced, whilst if the mutation is absent the PNA does not bind the DNA strongly enough to inhibit the shorter product PCR and both the longer and the shorter product are produced. Thus, the ineffectively blocked longer product PCR acts as an internal control verifying the use of proper conditions in the assay for the presence or absence of the mutation.

The invention includes a method wherein the presence of absence of each of a plurality of sequences within target nucleic acid sequence is detected in turn, by conducting a series of PCR amplification procedures using the same primer or primers and providing a respective nucleic acid analogue in each said procedure which is complementary to a respective one of said plurality of sequences to hybridise therewith to block said amplification procedure when said respective sequence is present but not otherwise.

Thus given a target sequence having a pair of spaced PCR primer binding sites, one on each strand, one can determine whether between those sites there occurs on one strand a particular specific sequence by providing a nucleic acid analogue capable of binding to the specific sequence to form a hybrid therewith which is stable under the PCR conditions and will thus block the exponential amplification. This principle may usefully be applied to determining which of a number of possible sequences are sequentially present in a region of nucleic acid within a gene or a larger region such as a gene cluster. By way of example, in $E.$ $Coli$ up to 30 genes are clustered in a short genetic region determining antibiotic resistance. To determine which antibiotic resistance genes are present in a particular organism would normally involve developing PCR primers for each gene of interest.

Using nucleic acid analogues for selective PCR blocking, one can determine the genes present using a single pair of primers which flank the entire region. Specific sequence nucleic acid analogues are made complementary to either strand for each gene sequence to be identified and the PCR reaction is tried with each nucleic acid analogue in turn present. When a sequence in the nucleic acid is present to which the analogue under test hybridises, the PCR reaction is blocked. Using conventional PCR, one would need a pair of primers specific for each sequence to be investigated. Each primer pair would need conditions in the amplification to be optimised by varying a number of parameters. As nucleic acid analogues of the kind described in the aforementioned PCT application are easily synthesised in desired sequences the problems of obtaining a large number of different PCR primers and developing amplification procedures suitable for each primer pair combination are overcome.

The invention includes a method of inhibiting the polymerase mediated extension of a primer hybridised to a nucleic acid template, comprising providing under hybridising conditions a nucleic acid analogue which forms a stable hybrid with the primer or with the template at the primer site or downstream from the primer site.

When the product of an amplification procedure is to be sequenced or to be detected and identified by probing with a labelled oligonucleotide, it will normally need to be obtained in single stranded form. The complementary strand will normally be present in equal quantities and the strands will tend to recombine. It is therefore desired to conduct PCR reactions in such a way as to produce predominantly one of the two product strands (asymmetric PCR). Currently, this is attempted by using more of one primer than of the other. Ideally, exponential production of desired sequence takes place until one primer is exhausted and linear amplification then results. Because of the unequal primer concentrations affecting the early stages of the reaction, there is often a problem in that the PCR process does not start properly.

Therefore, the present invention includes a method of conducting an asymmetric nucleic acid amplification procedure in which procedure each strand of a double stranded target nucleic acid has a region used as a template for a primer which is extended to form a second template complementary to said template, in which after a number of amplification cycles a nucleic acid analogue is added which hybridises to one of the primers sufficiently strongly to inhibit the hybridisation of said primer to its target under the conditions of the reaction, and said procedure is then continued through a number of further cycles Preferably, the amplification procedure is PCR.

The invention includes conducting an asymmetric amplification in this manner and then detecting or sequencing the product of the amplification.

The PNA concentration during the attempted PCR or other amplification reaction is preferably greater than 0.5 $\mu$M, preferably greater than 2.0 $\mu$M, most preferably more than 3 $\mu$M, e.g. 3 to 15 $\mu$M.

The nucleic acid analogue employed in all of the above is preferably a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms. However it may in general be any nucleic acid analogue capable of hybridising to a nucleic acid of complementary sequence to form a hybrid which is more stable against denaturation by heat than a hybrid between the conventional deoxyribonucleotide corresponding to said analogue and said nucleic acid. Preferably it is a nucleic acid analogue capable of hybridising to a double stranded nucleic acid in which one strand has a sequence complementary to said analogue, so as to displace the other strand from said one strand.

The separation of the nitrogen bearing atoms in the backbone of peptide nucleic acids defined above (PNA's) is preferably by five atoms. In nucleic acid analogues having the Formula I (below) this has been found to provide the strongest affinity for DNA. However, it may in some cases be desired to reduce the strength of binding between the PNA's and DNA by spacing one or more of the ligands by a less than optimal spacing, e.g. by a spacing of more than 5 atoms, e.g. by up to 14 atoms or more.

Preferably not more than 25% of interligand spacings will be 6 atoms or more. More preferably not more than 10 to 15% of interligand spacings will be 6 atoms or more. The aza nitrogen atoms which carry the ligands (directly or via linker groups) are not themselves counted in the spacings referred to above.

An alternative or additional method for reducing the strength of DNA binding is to omit certain of the ligands, putting in their place a moiety which contributes little or nothing to the binding of DNA, e.g. hydrogen. Preferably, not more than 25% of the ligand positions will be occupied by non-binding moieties, e.g. not more than 10 to 15%.

Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromouracil, azaadenines or azaguanines, etc.) attached to a peptide backbone through a suitable linker.

In preferred embodiments, the nucleic acid analogues used in the invention have the general formula (I):

(I)

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;

each of $A^1$–$A^n$ is a single bond, a methylene group or a group of formula (IIa) or (IIb):

where:
X is O, S, Se, $NR^3$, $CH_2$ or $C(CH_3)_2$;
Y is a single bond, O, S or $NR^4$;
each of p and q is an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio and amino;

each of $B^1$–$B^n$ is N or $R^3N^+$, where $R^3$ is as defined above;

each of $C^1$–$C^n$ is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $CR^6R^7$, $CH_2CR^6R^7$ or $CHR^6CHR^7$, where $R^6$ and $R^7$ are as defined above;

each of $G^1$–$G^{n-1}$ is in either orientation, where $R^3$ is as defined above;

Q is —$CO_2H$, —CONR'R", —$SO_3H$ or —$SO_2NR'R"$ or an activated derivative of —$CO_2H$ or —$SO_3H$; and I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers. Alternatively, C and D may be $CHR^6(CH_2)_S CHR^7$ where S may be from 0 to 2.

Preferred peptide nucleic acids have general formula (III):

(III)

wherein:

each L is independently selected from the group consisting of hydrogen, phenyl, heterocycles, e.g. of one, two or three rings, naturally occurring nucleobases, and non-naturally occurring nucleobases;

each $R^{7'}$ is independently selected from the group consisting of hydrogen and the side chains of naturally occurring alpha amino acids:

n is an integer from 1 to 60;

each of k, l and m is independently zero or an integer from 1 to 5; preferably the sum of k and m is 1 or 2, most preferably 1;

$R^h$ is OH, $NH_2$ or $-NHLysNH_2$; and $R^i$ is H or $COCH_3$.

Particularly preferred are compounds having formula (III) wherein each L is independently selected from the group consisting so the nucleobases thymine (T), adenine (A), cytosine (C), guanine (G) and uracil (U), in particular thymine, and n is an integer from 1 to 30, in particular from 4 to 20.

The peptide nucleic acids of the invention may be synthesized by adaptation of standard peptide synthesis procedures, either in solution or on a solid phase. The synthons used may be specially designed monomer amino acids or their activated derivatives, protected by standard protecting groups. The oligonucleotide analogues also can be synthesized by using the corresponding diacids and diamines.

Thus, the monomer synthons used to produce compounds for use on the invention may be selected from the group consisting of amino acids, diacids and diamines having general formulae:

(IV)

or (V)

or (VI)

wherein L, A, B, C and D are as defined above, except that any amino groups therein may be protected by amino protecting groups; E is COOH, CSOH, SOOH, $SO_2OH$ or an activated derivative thereof; and F is $NHR^3$ or $NPgR^3$, where $R^3$ is as defined above and Pg is an amino protecting group.

Preferred monomer synthons are amino acids having formula (VII):

(VII)

or amino-protected and/or acid terminal activated derivatives thereof, wherein L is selected from the group consisting of hydrogen, phenyl, heterocycles, naturally occurring nucleobases, non-naturally occurring nucleobases, and protected derivatives thereof; and $R^{7'}$ is independently selected from the group consisting of hydrogen and the side chains of naturally occurring alpha amino acids. Especially preferred are such synthons having formula (4) wherein $R^{7'}$ is hydrogen and L is selected from the group consisting of the nucleobases thymine (T), adenine (A), cytosine (C), guanine (G) and uracil (U) and protected derivatives thereof.

The production of such PNA's is described in detail in PCT application No. PCT/EP92/01220 referred to above.

This invention includes a kit for use in the conduct of a nucleic acid amplification reaction comprising a plurality of primers for said amplification and at least one nucleic acid analogue which has a sequence complementary to a sequence in one of said primers or to a target nucleic acid sequence to be amplified using said primers in said amplification reaction.

Such a kit may further comprise a polymerase or ligase for use in said amplification reaction to produce extension or ligation of said primers, e.g. a DNA polymerase such as Taq polymerase.

For use in a "3SR" type of procedure, the kits may further include any one or more of a reverse transcriptase, an RNA polymerase and a nuclease such as RNase H.

Generally, such kits may further include nucleotides, (some or all of dTTP, dCTP, dATP and dGTP), one or more of which may be labelled in any known or suitable manner, e.g. radio labelled. Reagents for detecting such labels may be included. Kits may further include one or more of buffers, salts, stabilising agents and nucleic acid recognition agents. These may be reagents which recognise specific sequences or reagents which recognise nucleic acids in a non-sequence specific manner, example of the former being oligonucleotides or nucleic acid analogues of the PNA type, optionally bearing detectable labels, and of the latter being antibodies to nucleic acids.

Suitable labels for use in the invention include radioisotope labels, enzyme labels, biotin, spin labels, fluorophores, chemiluminescence labels, antigen labels and antibody labels.

Kits may further include reagents for conducting a positive control experiment including a template for amplification using said primers to produce an amplification product different from that of said nucleic acid amplification reaction.

A kit may further include reagents for use in sequencing a nucleic acid amplification product, e.g. polymerase such as Taq polymerase and one or more dideoxynucleotides.

In the following examples, the PNAs all have a backbone derived from monomer synthons of Formula VII and in each case each L is one of the naturally occurring nucleobases represented in the usual way by A, C, G or T. The nomenclature employed follows that used in PCT No. PCT/EP92/01220 referred to above.

The invention will be further illustrated by the following specific examples in which reference is made to the attached drawings in which.

Figure 1:
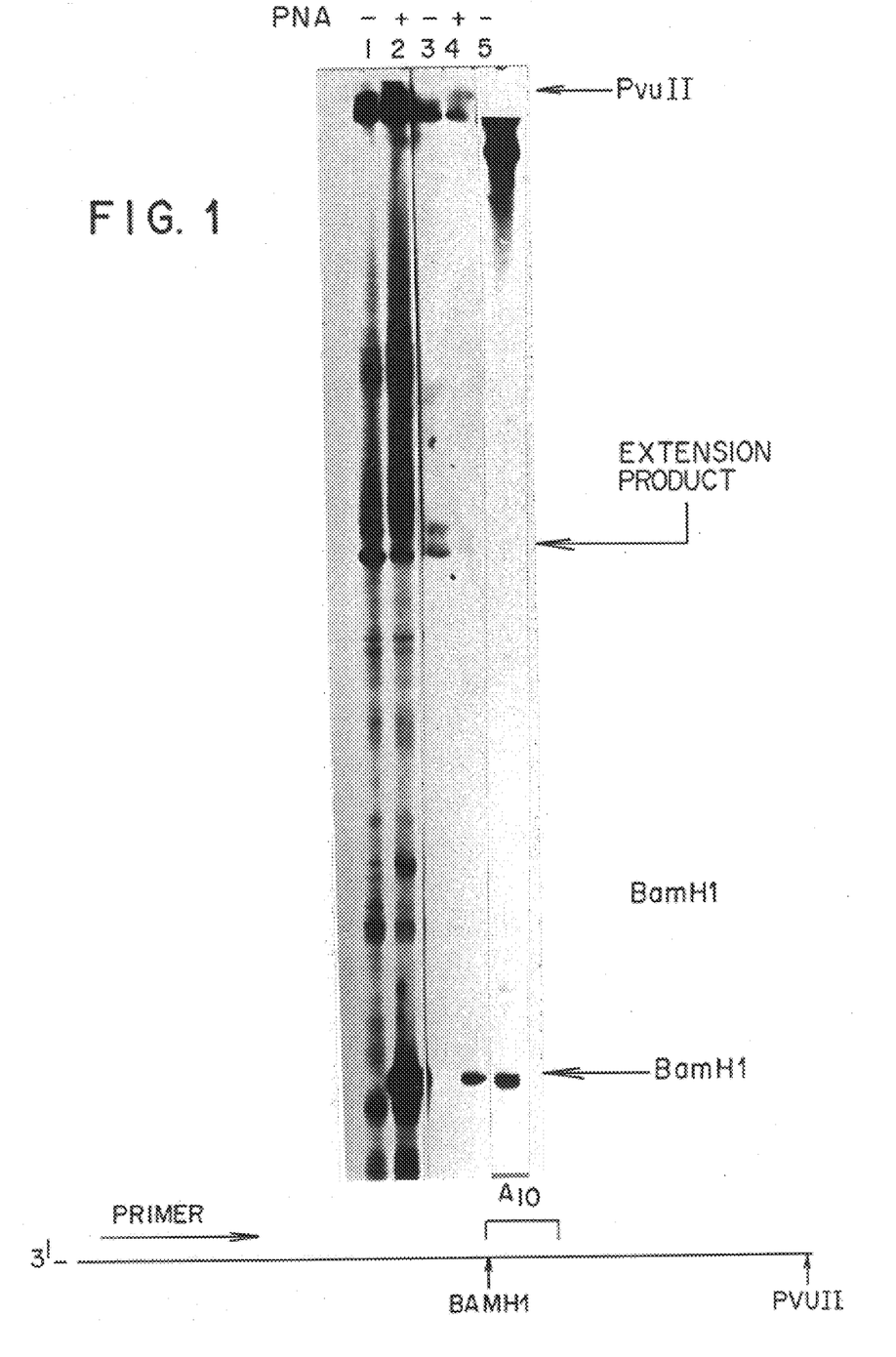
FIG. 1 is an autoradiograph of a gel showing inhibition of polymerase mediated extension of a primer by PNA.

EXAMPLE 1
Primer Extension Arrest by PNA 0.5 $\mu$g of a plasmid (Bluescript, Strategene, Inc) containing an inserted sequence of 10 thymine residues (pTlOKS) cleaved with the restriction endonuclease PvuII, and 0.1 $\mu$g "reverse primer" (5'-AAC AGC TAT GAC CAT G) to which was added 1 $\mu$l 10x concentrated buffer (for E. Coli Klenow DNA polymerase: 100 mM Tris-HCl, 100 mM MgCl$_2$, 50 mM NaCl, 1 mM dithiothreitol (DTT), pH 7.5, for Taq DNA polymerase: 100 mM Tris-HCl, 15 mM MgCl$_2$ 500 mM NaCl, 1 mg/ml gelatine, pH 8.3) and 6 $\mu$l H$_2$O and 100 ng of A$_{10}$ PNA complementary to the T$_{10}$ insert in the plasmid was incubated for 10 mins at 90° C., 60 mins at 37° C. and then cooled to 20° C. Then 1 $\mu$l of 10 mM DTT, 1 $\mu$l of 10 $\mu$M solution of dCTP, dGTP, dTTP, and 1 $\mu$Ci $\alpha^{32}$p-dATP and 1 U of the appropriate DNA polymerase was added. After 5 mins at 20° C. 2 $\mu$l of a 1 mM solution of dATP, dCTP, dGTP and dTTP was added and incubation was continued for 15 mins at 37° C. for E. coli DNA polymerase or 60° C. for Taq polymerase. The DNA was subsequently precipitated by addition of 50 $\mu$l ethanol, 2% (w/v) potassium acetate and analysed by electrophoresis in 8% (w/v) acrylamide/7M urea sequencing gel followed by autoradiography. The result is shown in FIG. 1, the lanes representing the following:

Lane 1: E. coli DNA polymerase Klenow fragment, no PNA.

Lane 2: as lane 1 but in the presence of PNA.

Lane 3: Taq polymerase, no PNA.

Lane 4: Taq polymerase in the presence of PNA.

Lane 5: control with plasmid cleaved with BamH1.

It can be seen from the diagram that the A$_{10}$ PNA should hybridise to one strand of the template DNA adjacent the Bam HI site. Thus if the A$_{10}$ PNA blocks polymerase extension of the primer, products should be produced which run on the gel with the Bam H1 cleavage products seen in lane 5. If polymerase extension is unchecked by PNA, longer extension products should be obtained. it can be seen that in each PNA containing lane (2 and 4) the expected band in the Bam Hl position is produced. In the absence of PNA, a longer product is seen which is substantially wholly absent in the PNA/Taq lane (lane 4) showing complete blocking of Taq by the PNA.

EXAMPLE 2
Detection of Single Base Mutation by PNA directed Inhibition of PCR DNA Amplification.

The plasmid pT10KS was constructed by cloning the complementary oligonucleotides 5'-GATCCT$_{10}$G and 5'-GATCCA$_{10}$G into respective strands at the BamHI site of the Bluescript KS+plasmid (Stratagene). The plasmid pT9CKS was constructed by cloning the complementary oligonucleotides 5'-TCGACT$_5$CT$_4$G and 5'-TCGACA$_4$GA$_5$G into the SalI site of pUCl9.

A polymerase chain reaction (PCR) was conducted which contained 25 ng plasmid 1, 25 ng plasmid 2 DNA, 1.25 mM DATP, 1.25 mM dCTP, 1.25 mM dGTP, 1.25 mM dTTP, 0.2 $\mu$g primer 1, 0.2 $\mu$g primer 2, and 2.5 $\mu$g PNA in 50 $\mu$l buffer (10 mM Tris-HCl, 3.5 mM MgCl$_2$, 50 mM KCl, 0.1 mg/ml gelatine, pH 8.3). The sample was heated to 94°C. for 5 mins, cooled to 65° C., at which stage 1 U of Taq DNA polymerase (Boehringer Mannheim) was added. Subsequently 30 temperature cycles (94° C. (2 mins), 40° C. (3 mins) and 65° C. (2 mins)) were run.

The resulting DNA was analysed by electrophoresis in 6% (w/v) polyacrylamide gels run in TBE buffer (90 mM Tris-borate, 1 mM EDTA, pH 8.3) and the DNA was visualised by staining with ethidium bromide.

Figure 2:
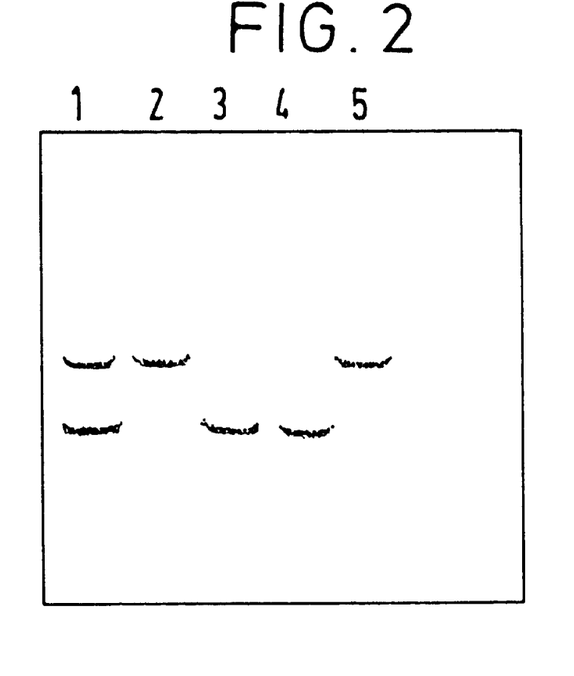
FIG. 2 is an ethidium bromide gel showing selective blocking of PCR reactions by PNA's discriminating between sequences differing by a single base pair.

The experiment was performed as described in Example 1 using "M13 primer" as primer 1 and "reverse primer" as primer 2. The resulting gel appears in FIG. 2. The following plasmids and PNAs were used:

Lane 1: pT9CKS (pBluescriptKS+ in which dA$_5$GA$_4$/ dT$_4$CT$_5$ PNA target was cloned into the Sal I site) and pT10KS (pBluescriptKS+in which a dA$_{10}$/dT$_{10}$PNA target was cloned into the Bam H1 site), no PNA.

Lane 2: as lane 1 but with PNA H-T$_5$CT$_4$LysNH$_2$.

Lane 3: as lane 1 but with PNA H-T$_{10}$LysNH$_2$.

Lane 4: pT10KS and pT9CKS with PNA H-T$_5$CT$_4$-LysNH$_2$.

Lane 5: pT10KS and pT9CKS with PNA H-T$_{10}$LysNH$_2$.

In lane 1, two PCR products are clearly seen, one from each plasmid. Amplification of pT10Ks gives a 118 bp fragment and amplification of pT9CKS gives a 221 bp fragment.

Plasmid pT9CKS contains a target sequence for PNA T$_5$CT$_4$LysNH$_2$. In lane 2 one sees no band for this plasmid showing inhibition of the PCR by the PNA.

EXAMPLE 3
Further Demonstration of PNA Directed Inhibition of PCR

The PNA T$_{10}$-LysNH$_2$ was synthesized as in Egholm, M., Buchardt, O., Nielsen, P. E. and Berg, R. H. (1992) J. Amer. Chem. Soc. 114, 1895–1897 and Egholm, M., Buchardt, O., Nielsen, P. E. and Berg, R. H. (1992) J. Amer. Chem. Soc. 114, 9677–9678. The plasmids pT10KS and pT9CKS were as described in Example 2. The control plasmid PCKS was constructed by cloning a 99 bp PCR fragment (with no target sites for any of the PNSa used in this example) into the SmaI site of the bluescript KS+plasmid. Using standard techniques plasmids were isolated from selected clones of recombinant E Coli JM103, purified by buoyant density centrifugation in CsCl gradients and sequenced by the dideoxy method.

The following oligonucleotide primers were used in the PCR reactions: reverse primer (5'-CACACAGGAAACAGCTATGAC)SEQ ID NO:2 and forward primer (5'-GTAAAACGACGGCCAGT)SEQ ID NO:3. PCR amplifications were carried out in a 50 $\mu$l volume containing 1 ng of each plasmid, 0.2 $\mu$M of each primer, 200 $\mu$M dNTP, 10 mM Tris-HCl, pH 8,3 (at 25° C.), 10 mM KCl, and 3 mM MgCl$_2$.

The PCR reactions were overlain with 2 drops of paraffin oil and incubated at 90° C. for 2 minutes before the amplification process were initiated by the addition of 3 U of the stoffel polymerase (Perkin Elmer Cetus). A LEP amplifier machine (IgG Biotech) was used in all experiments and PCR cycle profiles were 96° C., 2 min—55° C., 3 min—35° C., 1 min—65° C., 2 min—35 cycles.

To ensure that the formation of the PNA/DNA complexes preceded PCR primer binding and extension the normal 3 step PCR cycle was expanded with a distinct PNA annealing step at a temperature well above the $T_m$ of the PCR primers.

Figure 3:
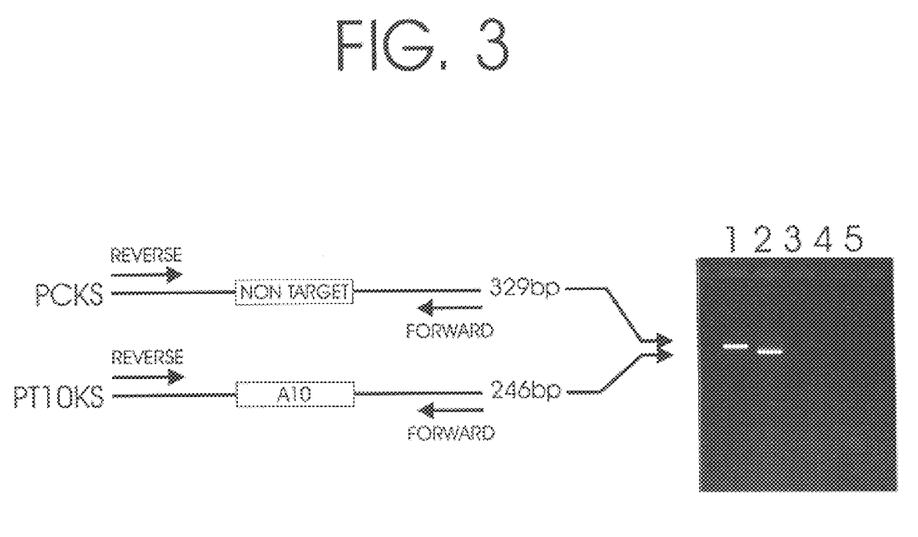
FIG. 3 is an ethidium bromide gel showing a further example of PNA directed inhibition of PCR.

FIG. 3 shows the experimental set-up and result of PCR inhibition in the presence of PNA $T_{10}$-LysNH$_2$. The two plasmid templates described above were used, namely the pT10KS plasmid which directs the amplification of a 246 bp fragment containing an $A_{10}$ target site and the control plasmid, pCKS, which directs the amplification of a 329 bp non-target fragment. When the PNA T10-LysNH$_2$ is absent (lane 2) the pT10KS plasmid directs the synthesis of the expected 246 bp PCR fragment. In the presence of 3.2 μM PNA $T_{10}$-LysNH$_2$, however, no product is produced (lane 3 to 5). The absence of product is not due to a non-specific inhibitory effect of PNA $T_{10}$-LysNH$_2$ on the PCR reaction, since PNA $T_{10}$-LysNH$_2$ will not inhibit the amplification of the expected 329 bp fragment from the pCKS control plasmid (lane 1). Thus, it is seen that the PNA $T_{10}$LysNH$_2$ can prevent the amplification of its cognate target DNA in a sequence specific manner.

EXAMPLE 4

Figure 4:
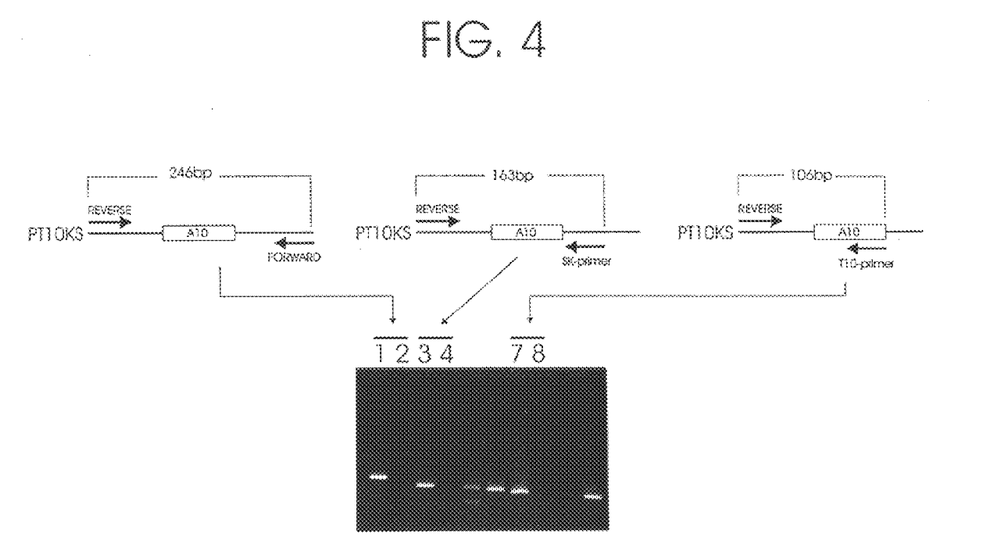
FIG. 4 is an ethidium bromide gel showing inhibition of PCR by PNA directed at sites on the PCR template which overlap with or are spaced by varying amounts from the primer target site.

Demonstration that the relative position of the PNA and PCR primer target sites can be changed without affecting inhibition This example shows the effects obtained where the PNA target site is (1) located in the middle of the PCR region, is (2) located immediately adjacent to a PCR primer site or (3) overlaps one of the PCR primer sites. There are fundamental differences between the underlying mechanisms of inhibition in these three cases. When the PNA target site is located at a distance from the PCR primer sites inhibition is expected to operate by preventing read-through by the polymerase. Conversely, inhibition is expected to operate by primer exclusion when the PNA and PCR primer target sites overlap. Finally, when the PNA target is located adjacent to the PCR primer site, inhibition is likely to operate by either preventing polymerase access to the PCR primer and/or by preventing initiation of primer elongation. In all three cases efficient inhibition can be obtained with PNA $T_{10}$-LysNH$_2$ as shown in FIG. 4. In this Example, PCR is attempted using, in respective runs, three different forward primers, referred to as "forward primer", "SK primer" and "A10 primer". These are forward primer (5'-GTAAAACGACGGCCAGT)SEQ ID NO: 3, T10 primer (5'-CATCCTTTTTTTTTTG) SEQ ID NO: 4 and SK primer (5'-TCTAGAACTAGTGGATC)SEQ ID NO: 5. In plasmid pT10 KS used in this example (see Example 2 for details) the 3'-end of the forward primer target site is located 101 bp downstream of the A10 target, the 3'-end of the SK primer is located immediately downstream of the A10 target and the A10 primer spans the A10 target site including 5 and 1 bp on the 5'- and 3'-side, respectively. Lanes 1–2: show amplification of the pT10KS plasmid with reverse and forward primers in the absence (1) or presence of 3.2 μM (2) of PNA-$T_{10}$-LysNH$_2$. Lanes 3 and 4: show amplification of the pT10KS with reverse and SK primers in the absence (3) or presence (4) of 3.2 μM of PNA $T_{10}$-LysNH$_2$. Lanes 7 and 8: shows amplification of the pT10KS plasmid with reverse and T10 primers in the absence (7) or presence (8) of 3.2 μM of PNA $T_{10}$-LysNH$_2$ PCR cycle conditions were 96° C., 2 min—55° C., 3 min—35° C., 1 min—65° C., 2 min—35 cycles. PNA $T_{10}$LysNH$_2$ will prevent formation of a PCR product from templates with widely spaced PNA and PCR primer target sites (lane 2), adjacent PNA and PCR primer target sites (lane 4) and overlapping PNA and PCR primer target sites (lane 8).

EXAMPLE 5

A PCR reaction was carried out generally as described in Example 2 in the absence and presence of a PNA complementary to one primer.

Figure 5:
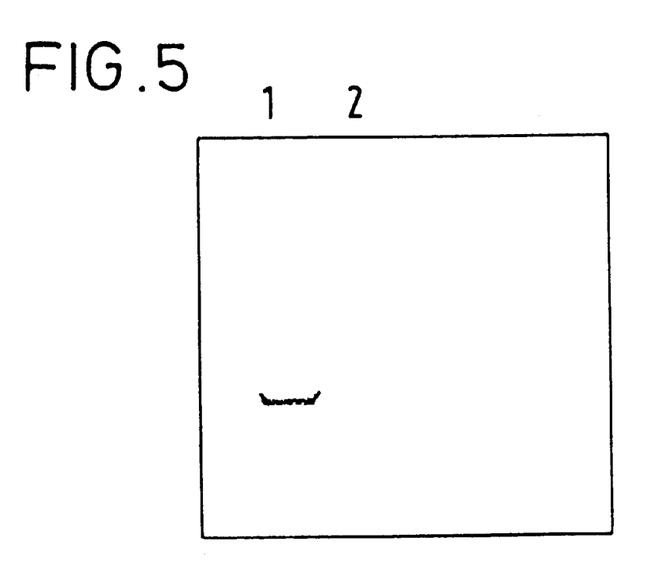
FIG. 5 is an ethidium bromide gel showing complete inhibition of a PCR reaction by PNA complementary to one primer.

The results are shown in FIG. 5. In lane 1, the expected PCR product is seen. In lane 2, the PCR reaction is shown to be entirely inhibited.

The example was carried out using "M13 primer" as primer 1 and GATCC $T_{10}$G as primer 2. The target plasmid was pT$_{10}$KS. The temperatures used in the second phase of each of the 30 cycles was 35° C. instead of 40° C.

EXAMPLE 6

PCR Inhibition with Mixed Sequence PNAs

Figure 6:
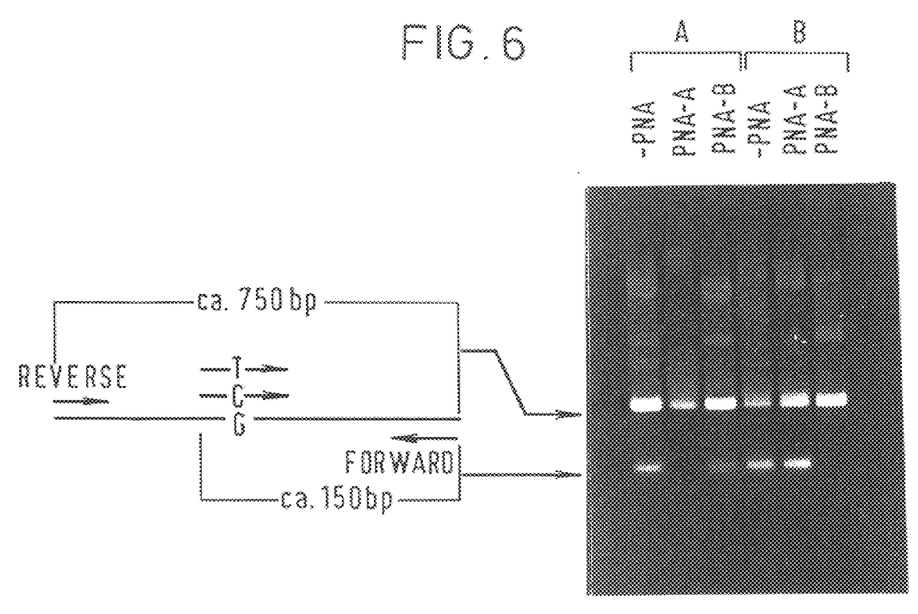
FIG. 6 is an ethidium bromide gel showing the result of Example 6 further illustrating PCR inhibition to identify a single base change.

The PNAs used in the previous examples contained only pyrimidine residues and have been shown to form triplexes with their target sequences. Thus, to show the generality of the principle a series of experiments were conducted with mixed sequence PNAs forming standard Watson-Crick duplexes with their target DNAS. FIG. 6 shows the experimental setup and result of single base mutation analysis with two mixed sequence PNAs differing by a single nucleotide (PNA-A: H-TTCCGG<u>T</u>TGCC—NH$_2$ and PNA-B: Gly-TTCCGG<u>C</u>TGCC—NH$_2$). Two templates are used ("A" and "B") containing the corresponding point mutation. Three oligonucleotide primers are involved in this experiment. A forward and reverse oligo pair which produce a 750 bp PCR fragment and a degenerate primer directed against the region containing the point mutation. Together with the forward primer the degenerate primer directs amplification of a 150 bp fragment using either the A or B allele as template. The PNAs are directed against the region containing the point mutation and clamping is thus expected to operate by primer exclusion.

In this example, each PCR reaction (50 μl) contains 200 μM dNTP, 10 mM Tris-HCl pH 9.9 (20° C.), 50 mM KCl, 1.5 mM MgCl$_2$, 0.01% gelatine, 0.1% Triton X-100, 1 U supertag enzyme (Stratagene) 1 ng of allele specific plasmid, 10 pmol of degenerate primer directed against the region containing the mutation, 10 pmol of forward primer, 10 pmol of reverse primer and PNAs as indicated. In the figure, the lanes are as follows: Lane 1: A-allele and no PNA. Lane 2: A-allele and 10 μM PNA-A. Lane 3: A-allele and 10 μM PNA-B. Lane 4: B-allele and no PNA. Lane 5: B-allele and 10 μM PNA-A. Lane 6: B-allele and 10 μM PNA-B. PCR conditions were 96° C. 1 min—60° C. 2 min—40° C. 30 sec—60° C. 2 min—30 cycles.

When the A-allele is used as template both the 750 bp (internal PCR control) and the 150 bp fragment (diagnostic of the allele) is produced in the absence of PNA-A (lane 1). When the reaction contains PNA-A, however, only the 750 bp PCR control fragment is produced (lane 2). In contrast, both the 750 bp and 5bp PCR fragments are produced in the presence of PNA-B (lane 3). Changing the template to the B-allele reverses the results. Thus, the presence of PNA-B will inhibit the production of the 150 bp fragment (lane 6) whereas the presence of PNA-A will not (lane 5). Thus, we conclude that both mixed sequence PNAs (A and B) are able to inhibit their cognate PCR product with point mutation accuracy.

We claim:

1. A method of inhibiting a nucleic acid amplification procedure, in which amplification procedure each strand of a double-stranded target nucleic acid has a region used as a first template for at least one primer which linked to another primer or extended with nucleotides to form a second template which is complementary to said first template, said method comprising hybridizing a nucleic acid analogue to a sequence of said first template or said at least one primer to inhibit linking or extension of the at least one primer during performance of the amplification procedure.

2. The method of claim 1, wherein the hybrid formed between the nucleic acid analogue and the sequence of said first template or said at least one primer is more stable against heat denaturation than a hybrid between a conventional nucleic acid corresponding to the nucleic acid analogue and the sequence of said first template or said at least one primer.

3. The method of claim 1, wherein the amplification procedure is a PCR or an LCR procedure.

4. The method of claim 1, further comprising, before said hybridizing step, conducting said amplification procedure in the absence of said nucleic acid analogue to accumulate amplification product.

5. The method of claim 4, wherein said nucleic acid analogue hybridizes to said amplification product.

6. A method of inhibiting amplification of a contaminating nucleic acid in an amplification procedure conducted using an amplification apparatus, in which amplification procedure each strand of a double-stranded nucleic acid has a region used as a first template for at least one primer which is linked to another primer or extended with nucleotides to form a second template which is complementary to said first template, said method comprising contacting a solution containing a nucleic acid analogue with said amplification apparatus to hybridize said nucleic acid analogue to any nucleic acid which may be present as a contamination to inhibit linking or extension of the contaminating nucleic acid during performance of the amplification procedure;

thereafter washing the amplification apparatus; and thereafter conducting said amplification procedure using said amplification apparatus, wherein amplification of the contaminating nucleic acid is inhibited by the hybridizing step.

7. The method of claim 6, wherein the hybrid formed between the nucleic acid analogue and the contaminating nucleic acid is more stable against heat denaturation than a hybrid between a conventional nucleic acid corresponding to the nucleic acid analogue and the contaminating nucleic acid.

8. A method of preventing a nucleic acid amplification product from serving as a template in a subsequent amplification procedure, in which subsequent amplification procedure each strand of a double-stranded nucleic acid has a region used as a first template for at least one primer which is linked to another primer or extended with nucleotides to form a second template which is complementary to said first template, said method comprising hybridizing a nucleic acid analogue to the nucleic acid amplification product to inhibit linking or extension of said amplification product during performance of the subsequent amplification procedure.

9. The method of claim 8, wherein the hybrid formed between the nucleic acid analogue and the nucleic acid amplification product is more stable against heat denaturation than a hybrid between a conventional nucleic acid corresponding to the nucleic acid analogue and the nucleic acid amplification product.

10. A method of inhibiting amplification of a contaminating nucleic acid in a subsequent amplification procedure conducted in an environment, in which subsequent amplification procedure each strand of a double-stranded nucleic acid has a region used as a first template for at least one primer which is linked to another primer or extended with nucleotides to form a second template which is complementary to said first template, said method comprising contacting a nucleic acid analogue with the environment to hybridize said nucleic acid analogue to any nucleic acid which may be present as a contamination to inhibit linking or extension of the at least one primer during performance of the subsequent amplification procedure; and thereafter conducting the subsequent amplification procedure, wherein amplification of the contaminating nucleic acid is inhibited by the hybridizing step.

11. The method of claim 10, wherein the hybrid formed between the nucleic acid analogue and the contaminating nucleic acid is more stable against heat denaturation than a hybrid between a conventional nucleic acid corresponding to the nucleic acid analogue and the contaminating nucleic acid.

12. A method of detecting the presence or absence of a target nucleic acid sequence, comprising (a) conducting an amplification procedure using (1) a double-stranded nucleic acid comprising a nucleic acid region, which nucleic acid region may contain the target nucleic acid sequence, (2) at least one primer, and (3) a nucleic acid analogue comprising a sequence which is complementary to said target nucleic acid sequence, wherein when the target nucleic acid sequence is present, then the nucleic acid analogue hybridizes with the target nucleic acid sequence to inhibit the at least one primer from linking to another primer or extending with nucleotides during performance of the amplification procedure, or when the target nucleic acid sequence is absent, then the at least one primer hybridizes with the nucleic acid region and is linked to another primer or extended with nucleotides to form an amplification product; and (b) determining the presence or absence of amplification product to detect the presence or absence of the target nucleic acid sequence.

13. The method of claim 12, wherein the hybrid formed between the nucleic acid analogue and the target nucleic acid sequence is more stable against heat denaturation than a hybrid between a conventional nucleic acid corresponding to the nucleic acid analogue and the target nucleic acid sequence.

14. The method of claim 12, wherein the target nucleic acid sequence, if present, is between a pair of primer binding sites, and the method comprises sequentially detecting the presence or absence of each of a plurality of sequences within the target nucleic acid sequence by conducting a series of amplification procedures using the same primers and different nucleic acid analogues for each of the series, each of which is complementary to a different one of the plurality of sequences, and determining whether amplification of each of the plurality of sequences has occurred to detect the presence or absence of the each sequence.

15. The method of claim 12, wherein the conducting step (a) further comprises including a control nucleic acid which undergoes amplification using the same at least one primer, to produce a second amplification product which is distinguishable from the amplification product comprising the nucleic acid region, and the determining step (b) further comprises determining the second amplification product.

16. A method of conducting an asymmetric nucleic acid amplification procedure, comprising providing a double-stranded nucleic acid, wherein each strand of the double-stranded nucleic acid has a region used as a first template for a first primer which is extended with nucleotides to form a second template which is complementary to said first template;

amplifying the double-stranded nucleic acid for a number of amplification cycles to produce amplification product;

combining the amplification product with a nucleic acid analogue which hybridizes to the first primer to inhibit extension of the first primer with nucleotides during performance of further amplification cycles, and continuing the amplification procedure for the further amplification cycles.

17. The method of claim 16, wherein the hybrid formed between the nucleic acid analogue and the first primer is more stable against heat denaturation than a hybrid between a conventional nucleic acid corresponding to the nucleic acid analogue and the first primer.

18. A method of inhibiting a polymerase-mediated extension procedure of a primer which is hybridized to a nucleic acid template, comprising providing an extension procedure reaction mixture comprising a nucleic acid template, a primer and a polymerase; and combining with the mixture a nucleic acid analogue which hybridizes to the primer or the nucleic acid template to inhibit extension of the primer with nucleotides during performance of the extension procedure.

19. The method of claim 18, wherein the hybrid formed between the nucleic acid analogue and the primer or the nucleic acid template is more stable against heat denaturation than a hybrid between a conventional nucleic acid corresponding to the nucleic acid analogue and the primer or the nucleic acid template.

20. The method of claim 1, wherein the nucleic acid analogue comprises a peptide nucleic acid.

21. The method of claim 6, wherein the nucleic acid analogue comprises a peptide nucleic acid.

22. The method of claim 8, wherein the nucleic acid analogue comprises a peptide nucleic acid.

23. The method of claim 10, wherein the nucleic acid analogue comprises a peptide nucleic acid.

24. The method of claim 12, wherein the nucleic acid analogue comprises a peptide nucleic acid.

25. The method of claim 16, wherein the nucleic acid analogue comprises a peptide nucleic acid.

26. The method of claim 18, wherein the nucleic acid analogue comprises a peptide nucleic acid.

* * * * *